ELM TREE
Filed May 31, 1974 2 Sheets-Sheet 1
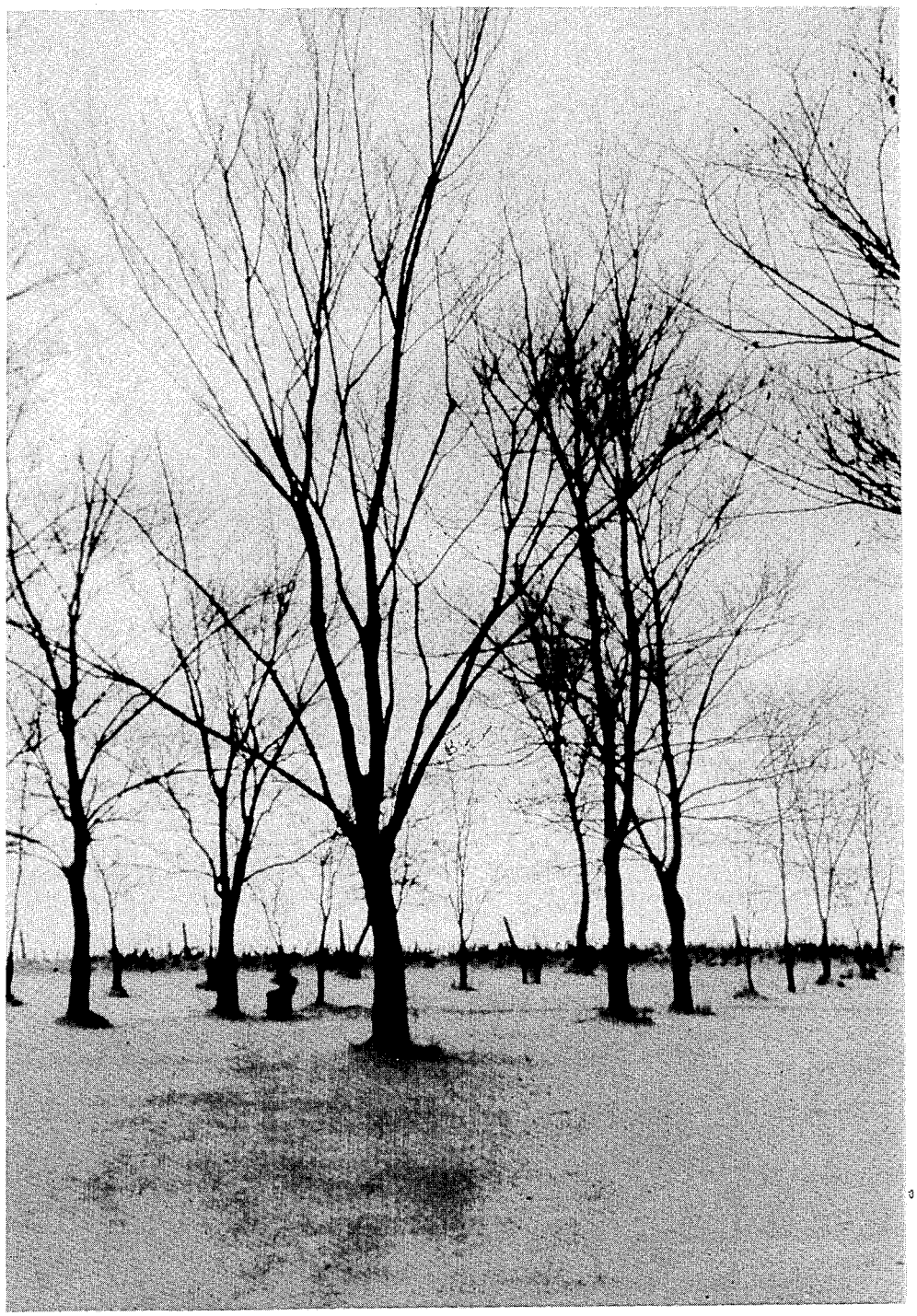

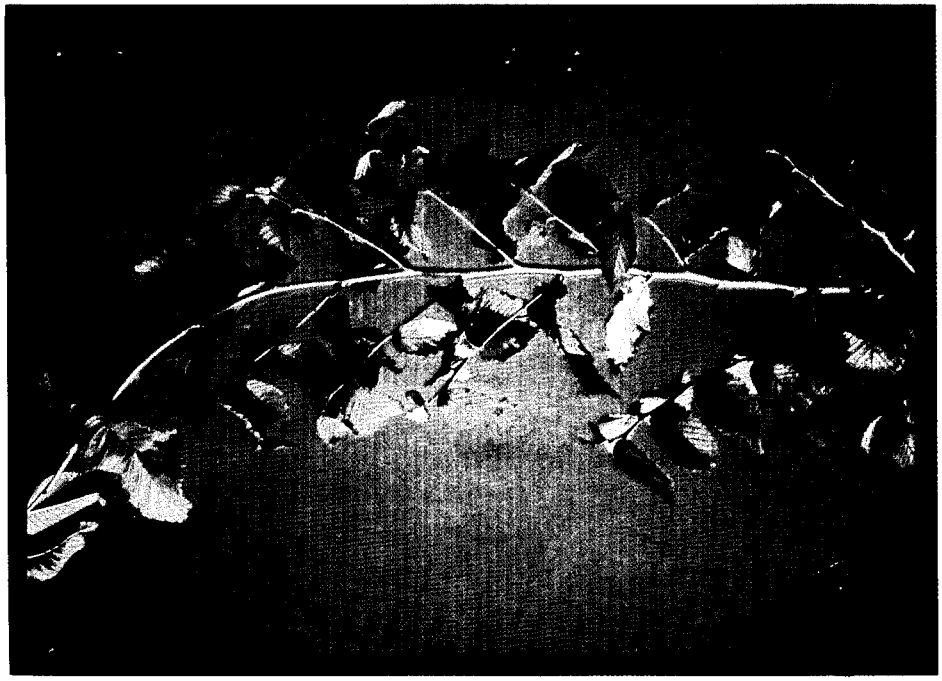
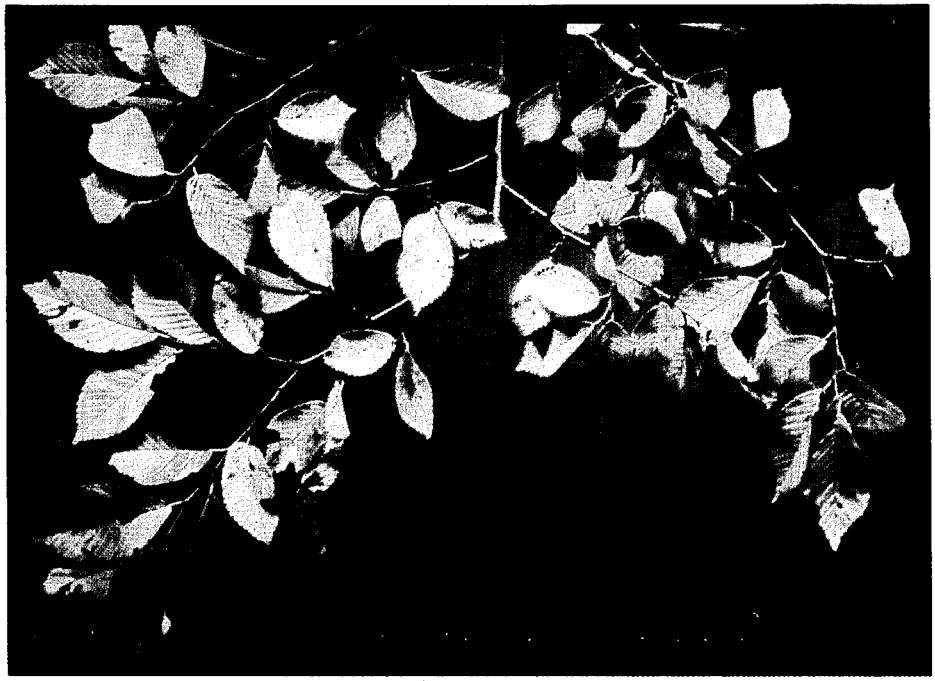

United States Patent

Plant Pat. 3,780

Patented Sept. 9, 1975

3,780

ELM TREE

Eugene B. Smalley, Cottage Grove, and Donald T. Lester, Madison, Wis., assignors to Wisconsin Alumni Research Foundation, Madison, Wis.

Filed May 31, 1974, Ser. No. 474,903

Int. Cl. A01h 5/12

U.S. Cl. Plt.—51 1 Claim

The present invention relates to a new and distinct variety of elm tree which is primarily distinguished by its high resistance to Dutch elm disease caused by *Ceratocystis ulmi* (Buism.) C. Moreau. The tree also shows a high tolerance to *Verticillium albo-atrum* Reincke and Berth., the causal agent of Verticillium wilt and has limited susceptibility to the blackleaf spot disease caused by *Gnomonia ulmea* (Schw.) Thum.

The tree is characterized by its rapid development in its early years to a densely foliated, upright form with a vase shaped crown and with a projected height at maturity of 18 to 20 meters. Budbreak takes place in southern Wisconsin in early May, the normal time in that locality for budbreak in the native American elm.

New growth on the developing, moderately-pubescent shoots is mineral green in color (R#31′) tinged on the upper surface of morocco red (R5#K) to brick red (R#5′K). As leaves mature they change first to a glossy Varley's green (R#31′m) and then to a mature forest green (R#29′m). The mature leaves exposed to full sun are nearly elliptical, obtuse and equal at the base, acuminate at the tip, doubly serrate at the leaf margins. 8.0–10.0 cm. long and 4.5 to 5.5 cm. wide, with shade leaves or leaves on highly vigorous sprouts being slightly larger. Leaves become a vivid, semi-transparent, pale greenish yellow (R#25d) to light greenish yellow (R#25b) in fall with this overall color holding well for many days prior to leaf drop. This tree has been named Sapporo Autumn Gold because of this fall coloration characteristic. (Color standards indicated are from Ridgway's color chart (Ridgway, R. 1912. Color standards and color nomenclature. Washington, D.C. 53 plates.))

Apical dominance is moderately strong resulting in limited side branch development on shoots of the current season, and usually beginning 30 to 60 cm. below the apex. Mature bark development progresses at a rate intermediate between the parents resulting in a smooth to lightly roughened bark whose weathered color ranges from dark to light mouse gray (R#15′′′′′b,k) to blackish brown (R#9′′′′m) underlaid in exposed cracks and new bark with a wood brown (R#17′′′) to Sanford's brown (R#11k) color. The inner bark is also a wood brown to Sanford's brown. Floral and seed characters are generally intermediate between the two parents. The original tree began flowering intensely at 5 years of age, somewhat earlier than is normally expected for either parent species.

The accompanying drawing shows a specimen tree of the new variety, as depicted in black and white to show its general form and habit of growth, with additional views in color to show new growth and the autumn coloration for which the tree variety has been named.

*Origin*

The "Sapporo Autumn Gold" elm is derived from open-pollinated seed collected from a single Siberian elm, *U. pumila* L., growing in the Botanical Garden of Hokkaido University, Sapporo, Japan. The maternal parent's location in the botanical garden, the physical traits of the progeny, and controlled hybridization experiments (see references 2 and 3 in E. B. Smalley et al., Hortscience, Vol. 8(6), December 1973, p. 514) leave little doubt that the tree is an $F_1$ hybrid between *U. pumila* and *U. japonica* (Rehd.) Sarg.

*Asexual Reproduction*

The "Sapporo Autumn Gold" elm cultivar can be propagated from root cuttings allowed to sprout in the greenhouse in moist sphagnum peat. Hormone treated sprouts can be transplanted as rooted cuttings after approximately 20 days in a perlite-peat rooting medium under fine intermittent mist.

*Determination of Resistance to Dutch Elm Disease*

As a broad approach to identifying hardy elms with low disease susceptibility elm seed imported from many parts of the world was grown for one year in the seedbed, transplanted into the field the second season, maintained under clean cultivation, and artificially inoculated with *Ceratocystis ulmi* in the third or fourth year. The inoculum contained approximately $10^5$ spores/ml. and was a mixture of spores from 10–15 different Wisconsin isolates of the fungus. Trees were inoculated in one-year-old wood in the upper crown. The survivors of this procedure were then reinoculated at least two or more times in subsequent years. As a final test (called the seasonal susceptibility test), selected resistant clones having ornamentally desirable features were clonally propagated in large numbers, grown in randomized field plantings for one or two years, and different individuals of each clone inoculated at the intervals indicated in the table below. In this test,

SEASONAL SUSCEPTIBILITY OF SELECTED ELM CLONES TO DUTCH ELM DISEASE

Percent crown damage at final reading (7/5 and 6/72) [a] [b]

| Elm species [c] | Clone No. | 1971 dates of inoculation | | | | | | | | | | |
|---|---|---|---|---|---|---|---|---|---|---|---|---|
| | | 4/28 | 5/12 | 5/18 | 5/25 | 6/1 | 6/7 | 6/14 | 6/21 | 7/6 | 7/19 | 8/2 |
| *Ulmus Americana* | 185–1 | 0 | 23.4 | 28.1 | 29 | 69.6 | 62.1 | 70.1 | 90.1 | 100 | 40 | 0 |
| | 185–2 | 0 | 0 | 2.5 | 29.8 | 82.8 | 79 | 100 | 81 | 37 | 58.3 | 0 |
| | 185–3 | 33.3 | ------ | 48.0 | 7 | 53.3 | 80 | ------ | 97.5 | 100 | 65 | ------ |
| | 185–4 | ------ | ------ | ------ | ------ | ------ | ------ | 31.7 | 100 | ------ | ------ | ------ |
| | 185–5 | ------ | ------ | ------ | 50 | 100 | 100 | ------ | 100 | ------ | 37.5 | ------ |
| | 411–3 | 75 | 62.6 | 100 | 60 | 100 | 100 | 100 | 95.8 | 99.2 | 97.2 | 0.7 |
| | 412–1 | 66.7 | 86.2 | 91.7 | 89.6 | 88.3 | 79.73 | 100 | 100 | 100 | 88.9 | 0.5 |
| *Ulmus Pumila* × *Ulmus Japonica* | 44–11 | 0 | 0 | 0 | 0 | 7.5 | 0 | 0 | 6.8 | 0 | 0 | 0 |
| | 44–25 | ------ | ------ | 0 | ------ | 0 | ------ | 0 | ------ | ------ | ------ | ------ |

[a] Elm clones all derived from trees previously symptomless following one or more inoculations with Wisconsin strains of *Ceratocystis ulmi*.

[b] Mixed inoculum consisted of a conidial suspension prepared from isolates of *C. ulmi* from Wisconsin, Kansas, Massachusetts, Illinois, Nebraska, Minnesota, New York, Connecticut, and Maine.

[c] Trees planted as vigorous rooted cuttings in 1970, 3 plants per clone per block, 25 randomized clones per block (with some clones occasionally missing), and 40 blocks.

inoculum consisted of a mixed conidial suspension from 10 different isolates of the fungus from different North American locations. Observations on disease development were then recorded periodically through the year following inoculation.

The cultivar of this application, named Sapporo Autumn Gold, possessed superior resistance to *C. ulmi* as shown in the table above.

What is claimed is:

1. A new and distinct variety of elm tree as herein described and illustrated primarily characterized by its high resistance to Dutch elm disease.

No references cited.

ROBERT E. BAGWILL, Primary Examiner